(12) United States Patent
Yavagal

(10) Patent No.: US 10,518,051 B2
(45) Date of Patent: Dec. 31, 2019

(54) CLOSED AUTOMATED SUCTION DEVICE AND METHOD

(71) Applicant: Dileep Yavagal, Coral Gables, FL (US)

(72) Inventor: Dileep Yavagal, Coral Gables, FL (US)

( * ) Notice: Subject to any disclaimer, the term of this patent is extended or adjusted under 35 U.S.C. 154(b) by 731 days.

(21) Appl. No.: 14/052,181

(22) Filed: Oct. 11, 2013

(65) Prior Publication Data

US 2014/0102441 A1 Apr. 17, 2014

Related U.S. Application Data

(60) Provisional application No. 61/712,289, filed on Oct. 11, 2012.

(51) Int. Cl.
*A61M 16/04* (2006.01)
*A61M 16/00* (2006.01)

(52) U.S. Cl.
CPC .... *A61M 16/0463* (2013.01); *A61M 16/0057* (2013.01); *A61M 16/0488* (2013.01); *A61M 16/0434* (2013.01); *A61M 16/0461* (2013.01); *A61M 16/0465* (2013.01)

(58) Field of Classification Search
CPC .......... A61M 16/0057; A61M 16/0434; A61M 16/0461; A61M 16/0463; A61M 16/0465; A61M 16/0468; A61M 16/0488; A61M 16/0816
USPC ..................................................... 128/207.14
See application file for complete search history.

(56) References Cited

U.S. PATENT DOCUMENTS

| | | | | |
|---|---|---|---|---|
| 4,646,733 A * | 3/1987 | Stroh | ................... | A61M 16/042 128/204.21 |
| 5,167,622 A * | 12/1992 | Muto | ................ | A61M 16/0463 604/35 |
| 5,832,920 A * | 11/1998 | Field | ..................... | A61M 16/04 128/205.12 |
| 6,460,540 B1 * | 10/2002 | Klepper | ............ | A61M 16/0463 128/207.14 |
| 6,725,862 B2 * | 4/2004 | Klinberg | ........... | A61M 16/0463 128/207.14 |
| 7,258,120 B2 * | 8/2007 | Melker | ................. | A61M 16/04 128/207.14 |
| 7,503,328 B2 * | 3/2009 | Kolobow | .......... | A61M 16/0463 128/200.26 |
| 8,439,041 B2 * | 5/2013 | Lally | ..................... | A61M 16/04 128/207.14 |
| 8,591,496 B2 * | 11/2013 | Caruso | .............. | A61M 16/0463 128/207.14 |
| 2007/0227543 A1 * | 10/2007 | Peichel | ................. | A61M 25/00 128/207.14 |
| 2008/0011304 A1 * | 1/2008 | Stewart | ................. | A61M 16/04 128/207.15 |

(Continued)

*Primary Examiner* — Bradley H Philips
*Assistant Examiner* — Victoria Murphy
(74) *Attorney, Agent, or Firm* — Allen Dyer Doppelt & Gilchrist PA

(57) ABSTRACT

A closed automated suction device (CASD) is described. The device is designed to overcome the need for manual suction and to facilitate strict asepsis in patients who are endotracheally intubated or tracheostomied. The device includes an outer tube with an inner tube concentrically nested within to define a cavity therebetween. The inner tube comprises a passage extended therethrough for providing ventilation, and the cavity between the inner and outer tubes is configured for communication with a vacuum source to provide aspiration.

10 Claims, 2 Drawing Sheets

(56) References Cited

U.S. PATENT DOCUMENTS

2011/0282326 A1* 11/2011 Krupa ................ A61M 1/0031
604/540
2012/0247473 A1* 10/2012 Fendler ............. A61M 16/0463
128/205.27

* cited by examiner

CLOSED AUTOMATED SUCTION DEVICE AND METHOD

CROSS-REFERENCE TO RELATED APPLICATION

This application claims the benefit of U.S. Provisional Patent Application Ser. No. 61/712,289, filed Oct. 11, 2012, the contents of which are incorporated by reference herein.

FIELD OF INVENTION

The present invention generally relates to the field of endotracheal intubation and tracheostomy devices, and more particularly, to an endotracheal intubation and tracheostomy device and method for providing aspiration and ventilation in a closed system.

BACKGROUND

Of those patients who die in a medical intensive care unit (MICU), approximately 33% succumb to nosocomial pneumonia. Patients who are endotracheally intubated or tracheostomied for greater than 72 hours are especially prone to developing nosocomial pneumonia. The situation is further exacerbated when these patients are placed on artificial ventilation.

The most prominent factors that contribute to the pathogenesis of nosocomial pneumonia include: (1) mechanical impediment to mucocilliary clearance of lower respiratory tract secretions by cuffed endotracheal and trachostomy tubes at the level of the trachea; (2) colonization of the tracheabronchi with organisms from hands of health care workers; and (3) microaspiration via small leaks around cuffed endotracheal or tracheostomy tubes from the oropharynx into the respiratory tract.

Presently, repeated manual suction through the endotracheal/tracheostomy tubes facilitates clearing and aids in the prevention of stagnation of lower respiratory tract secretions. This is unfortunately effective only to a limited extent, as this process involves a high risk of introduction of organisms from health care workers in the upper respiratory tract, despite stringent sterilization efforts. An additional problem is the waste of valuable manpower as suction must be frequent to be effective.

SUMMARY OF THE INVENTION

In view of the foregoing background, an object of the present invention is to provide a closed automated suction device (CASD) designed to overcome the need for manual suction and to facilitate strict asepsis in patients who are endotracheally intubated or tracheostomied.

According to an aspect of the present invention, an endotracheal device, also referred herein as the CASD, (for insertion into the trachea via intubation or tracheostomy) comprises an outer tube and an inner tube, the inner tube concentrically nested within the outer tube to define a cavity therebetween, and the outer and inner tubes collectively have corresponding first and second ends with the inner tube having a passage extended therethrough. The first and second ends of the inner tube are configured to provide airway maintenance for a patient. The outer tube is configured for communication with a vacuum source such that suction is generated within the cavity for evacuation of respiratory secretions from a patient. The inner tube is preferably configured to engage a ventilator at the first end, and the second end is configured for intubation, to supply air to the respiratory system of an intubated/tracheostomied patient.

In some embodiments, the cavity between the inner and outer tubes of the endotracheal device is closed proximate the first end. Furthermore, a side tube may project from the outer tube proximal to the first end, the side tube comprising an inner cavity therein continuous with the cavity between the inner and outer tubes. The outer tube is configured for communication with the vacuum source via the side tube. The device may also include a collector inline with the side tube and the vacuum source, for trapping respiratory secretions. The device may also include an inflatable cuff surrounding the outer tube for providing a seal between the device and the tracheobronchial tree.

According to a method aspect of the present invention, a method for endotracheal intubation and aspiration comprises inserting the endotracheal device described herein in to the trachea of a patient. The insertion may be by nasotracheal insertion, orotracheal insertion, and/or tracheostomal insertion. Furthermore, ventilation is provided to the trachea via the passage extending through the inner tube, and aspiration of secretions from the trachea is provided via the cavity between the inner and outer tubes.

These and other objects, aspects and advantages of the present invention will be better appreciated in view of the drawings and following detailed description of preferred embodiments.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION OF EMBODIMENTS

Figure 1:
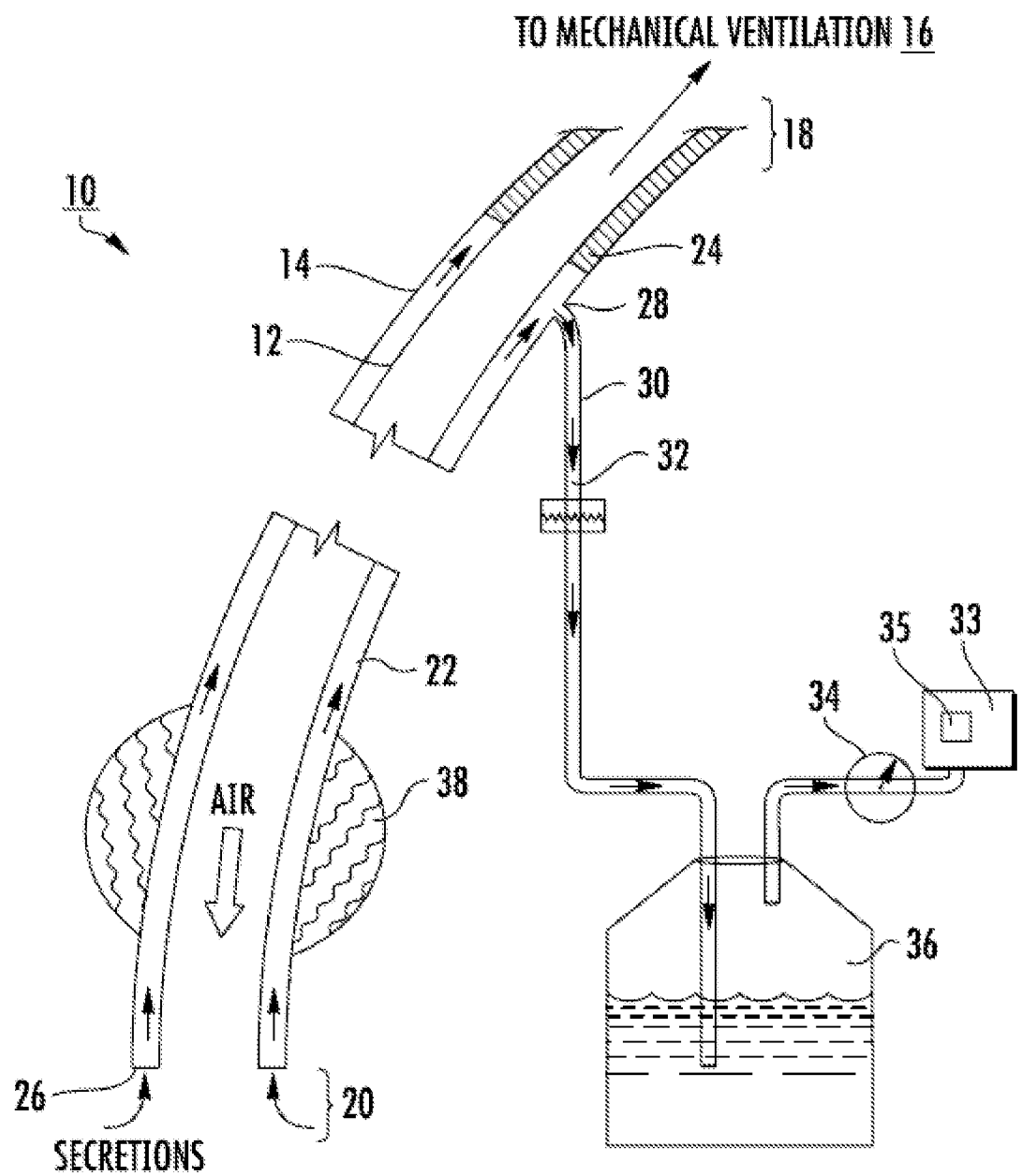
FIG. 1 illustrates an example of an embodiment of a closed automated suction device.

Reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The terminology used herein is for the purpose of describing particular embodiments only and is not intended to be limiting of the invention. As used herein, the indefinite articles "a" "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "comprises" is used herein to mean that other elements, steps, etc. are optionally present. When reference is made herein to a method comprising two or more defined steps, the steps can be carried out in any order, or simultaneously (except where the context excludes that possibility), and the method can include one or more steps which are carried out before any of the defined steps, between two of the defined steps, or after all of the defined steps (except where the context excludes that possibility).

As used herein, the terms "including", "includes", "having", "has", "with", or variants thereof, are intended to be inclusive similar to the term "comprising."

In this section, the present invention will be described more fully with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art.

As used herein, a "patient" refers to any animal, inclusive of a human, in need of medical care that involves the need for endotracheal intubation and/or tracheostomy.

The present invention is directed to a closed automated suction device (CASD) designed to overcome the need for manual suction and to facilitate strict asepsis. This and other objects, features, and advantages in accordance with the present invention are provided by a device having two concentric tubes: an inner tube that is used for connecting a ventilator to the patient's respiratory system, and an outer tube that defines a space between the inner and outer tube. The space between the two tubes is used for suction. The respiratory secretions are thus suctioned from the lower end of the suction vent to the side tube into a suction bottle.

The present invention provides controlled ventilation and aspiration and allows the suction force to be transmitted through a closed system, eliminating the need to disconnect the ventilator each time suction is needed. Additionally, the frequency and intensity of suction is controlled by a regulator and controller, such that respiratory secretions are suctioned from the patient in a controlled and automated fashion.

Referring initially to FIG. 1, the CASD, or endotracheal device, 10 ("the device" comprises to tubes, an inner tube 12 and an outer tube 14, of differing diameters that are concentrically nested to define a cavity 22 therebetween, the tubes being for insertion into the trachea of a patient. The tubes 12, 14 collectively define the first 18 and second 20 ends of the device 10. In a preferred embodiment, the difference in diameter between the two tubes is about 1.5 mm to about 4 mm. The tubes 12, 14 are made from at least one of latex, polyvinyl chloride, silicone rubber, wire-reinforced tubing, stainless steel, and any other material known in the art.

The inner tube 12 defines a passage extending therethrough and is used as a conduit to supply air to a patient's respiratory system, and is thus connected to a ventilator 16 on the device's first end 18. The second end 20 of the device is configured for intubation, or placed into a patient's trachea, to maintain an open airway or to serve as a conduit through which to administer certain drugs. The outer tube 14 is also configured for communication with a vacuum source 33.

The cavity 22 defined between the inner tube 12 and outer tube 14 is used for suction, and evacuates respiratory secretions from the patient, and is thus also referred to as a "concentric suction space" (CSS). The CSS 22 is closed 24 proximate the first end 18 of the device 10, such that no cavity extends therefrom. The CSS 22 opens 26 proximate the second end 20 of the device 10 for providing an opening for secretions to enter and continue towards the first end 18. At a junction 28, a side tube 30 projects from the outer tube 14 proximal to the first end 18. The side tube 30 is preferably about 3 mm to about 10 mm in diameter; however, the diameter could be any size dependent on the necessary suction forces needed and as would be understood by those skilled in the art. The inner cavity 32 of the side tube 30 is continuous with the cavity 22, and the side tube 30 is configured to engage a vacuum source 33.

In a preferred embodiment, a vacuum force regulator 34 that communicates with both the side tube 30 and the vacuum source 33 limits the intensity of suction. Respiratory secretions are thus suctioned from the second end 20 of the device 10, through the CSS 22, and into the side tube 30.

The vacuum frequency and intensity regulated by the vacuum force regulator 34 is preferably controlled by an electronic controller 35. For example, higher frequency of suctioning may be set on the controller 35 to prevent accumulation of secretions in the CSS 22.

A collector 36 is positioned inline, between the side tube 30 and the vacuum 33 so that respiratory secretions are trapped in the collector 36, and do not enter the device responsible for creating the vacuum 33. In a related embodiment, the CSS 22 is bolstered with material that spans between the inner tube 12 and the outer tube 14 to prevent the CSS 22 from collapsing onto itself due to suction forces.

In some embodiments, the CASD 10 comprises an inflatable cuff 38 surrounding the outer tube 14 to seal the tracheobronchial tree of the patient against leakage of respiratory gases and pulmonary aspiration of gastric contents, blood, secretions and other fluids.

Figure 2:
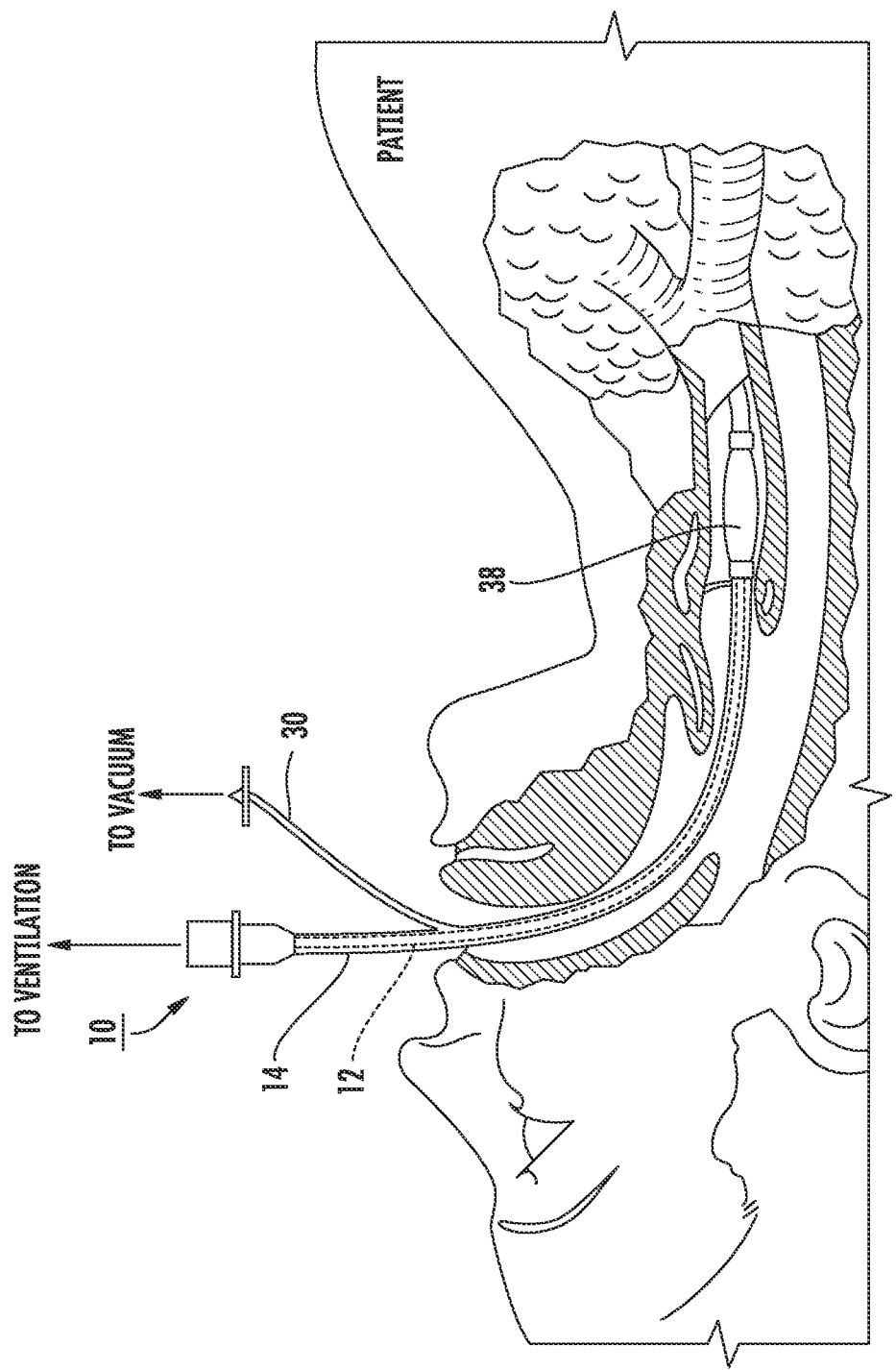
FIG. 2 illustrates an example of an embodiment of a closed automated suction device utilized in a patient.

FIG. 2 illustrates the CASD 10 as inserted into the trachea of a patient orotracheally (by mouth). However, as it would be understood by those skilled in the art, the CASD 10 may also be inserted by nasotracheal (nasal) insertion and/or tracheostomal insertion.

In another aspect of the present invention, a method for endotracheal intubation and aspiration in a patient is provided. The method includes inserting an endotracheal device into the trachea such that an inner tube of the device is concentrically nested within an outer tube of the device to provide a cavity therebetween. The outer and inner tubes collectively have corresponding first and second ends, wherein the cavity between the inner and outer tubes is closed proximate the first end. Also, the inner tube has a passage extended therethrough.

The method may further include ventilating the patient by allowing air into a passage extending through the inner tube. Ventilation may also be provided by a ventilator being connected to the first end of the device at the inner tube.

The method also includes aspirating secretions from the trachea by applying vacuum to the cavity between the outer and inner tubes of the device. Vacuum may be applied via a side tube projecting from the outer tube, the side tube being in communication with a vacuum source.

The insertion step is accomplished by nasotracheal insertion, orotracheal insertion, and/or tracheostomal insertion. Furthermore, the method includes providing ventilation into the trachea via the passage extending through the inner tube of the device, and aspirating secretions from the trachea via the cavity between the inner and outer tubes. The aspiration may be controlled by vacuum regulation of the vacuum source such that the aspiration rate is appropriate for the amount of respiratory secretions being produced within the patient.

Overall, the CASD 10 significantly advances the standard of care for mechanically ventilated patients by providing for closed and automated suction of their respiratory tract secretions with endotracheal and tracheostomy tubes. The use of the CASD described herein for suction of respiratory tract secretions in mechanically ventilated patients has two very significant advantages over the conventional suction method. First, it maintains strict asepsis as there is no need for opening the ventilation system from the ventilator to the patient each time suction is needed. Second, it eliminates the need for precious man-hours spent on suction.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for endotracheal intubation and aspiration of secretion in a patient, comprising:
    inserting an endotracheal device into a trachea of the patient, the endotracheal device having an inner tube concentrically nested and integrated within an outer tube of the endotracheal device to form an annulus cavity therebetween, the annulus cavity extending continuously around, and being concentric with approximately an entire length of the inner tube and being open at a distal end of the endotracheal device;
    connecting the annulus cavity to a vacuum source via a side tube projecting from the outer tube that is in communication with the vacuum source, wherein the annulus cavity is closed above the side tube;
    providing a bi-directional flow inside the inner tube using a ventilator coupled to an upper end of the inner tube of the endotracheal device where the annulus cavity is closed and the ventilator being separate and operating independently from the vacuum source connected to the annulus cavity;
    aspirating the secretion from the trachea of the patient by applying a vacuum to the annulus cavity formed between the outer and inner tubes of the device using the vacuum source that is separate from the ventilator and aspirating contemporaneously with the ventilator separately providing the bi-directional flow inside the inner tube ventilating the patient;
    adjusting a regulator connector to the vacuum source to adjust at least one of a frequency and an intensity of the aspirating the secretion from the trachea; and
    trapping the secretion being aspirated from the trachea out through the annulus cavity in to a collector.

2. The method of claim 1, wherein the inserting step is accomplished by nasotracheal insertion.

3. The method of claim 1, wherein the inserting step is accomplished by orotracheal insertion.

4. The method of claim 1, wherein the inserting step is accomplished by tracheostomal insertion.

5. A method for endotracheal intubation and aspiration of secretion in a patient using an endotracheal device comprising an inner tube concentrically nested and integrated within an outer tube to form an annulus cavity therebetween, the annulus cavity extending continuously around and approximately an entire length of the inner tube and being open at a distal end of the endotracheal device, the method comprising:
    coupling the inner tube to a ventilator;
    coupling the annulus cavity to a vacuum source that is separate from the ventilator via a side tube projecting from the outer tube that is in communication with the vacuum source, wherein the annulus cavity is closed above the side tube;
    inserting the endotracheal device into a trachea of the patient;
    providing a bi-directional flow inside the inner tube using the ventilator coupled to the inner tube of the endotracheal device where the annulus cavity is closed and operating independently from the vacuum source coupled to the annulus cavity;
    aspirating the secretion from the trachea of the patient by applying a vacuum to the annulus cavity using the vacuum source that is separate from the ventilator and aspirating contemporaneously with the ventilator separately providing the bi-directional flow inside the inner tube ventilating the patient; and
    trapping the secretion being aspirated from the trachea out through the annulus cavity in to a collector.

6. The method of claim 5, wherein the difference between an inner diameter of the inner tube and an inner diameter of the outer tube is about 1.5 mm to about 4 mm.

7. The method of claim 5, wherein a proximal end of the inner tube extends beyond a distal end of the outer tube of the endotracheal device.

8. The method of claim 5, wherein the inserting step is accomplished by nasotracheal insertion.

9. The method of claim 5, wherein the inserting step is accomplished by orotracheal insertion.

10. The method of claim 5, wherein the inserting step is accomplished by tracheostomal insertion.

* * * * *